(12) United States Patent
Chao

(10) Patent No.: US 6,869,438 B2
(45) Date of Patent: Mar. 22, 2005

(54) GASTRIC PARTITION CLIP

(76) Inventor: Seh-Huang Chao, 4F-1, No. 6, Lane 169, Sec. 1, Daan Rd., Daan Chiu, Taipei City (TW)

( * ) Notice: Subject to any disclaimer, the term of this patent is extended or adjusted under 35 U.S.C. 154(b) by 0 days.

(21) Appl. No.: 10/352,649

(22) Filed: Jan. 27, 2003

(65) Prior Publication Data

US 2004/0147942 A1 Jul. 29, 2004

(51) Int. Cl.$^7$ .............................................. A61B 17/08
(52) U.S. Cl. ...................................................... 606/153
(58) Field of Search ................................ 606/120, 151, 606/153, 155, 156, 157, 221; 132/276, 280; D24/143; 24/570, 571, 545, 564, 566, 485, 488

(56) References Cited

U.S. PATENT DOCUMENTS

| | | | | | |
|---|---|---|---|---|---|
| 20,412 A | * | 6/1858 | Elst | ............................. | 188/123 |
| 2,536,448 A | * | 1/1951 | Klar | ............................. | 132/276 |
| 2,583,784 A | * | 1/1952 | MacCaferri | ................. | 223/91 |
| 2,659,378 A | * | 11/1953 | Caseta | ........................ | 132/276 |
| 4,274,415 A | * | 6/1981 | Kanamoto et al. | ........... | 606/142 |
| 4,343,321 A | * | 8/1982 | Caranicas | .................... | 132/276 |
| 4,378,802 A | * | 4/1983 | Ersek | .......................... | 606/157 |
| 5,334,209 A | * | 8/1994 | Yoon | ........................... | 606/141 |
| 5,634,932 A | * | 6/1997 | Schmidt | ..................... | 606/157 |
| 6,187,020 B1 | * | 2/2001 | Zegdi et al. | ................. | 606/153 |
| 6,189,187 B1 | * | 2/2001 | Williams | ...................... | 24/563 |
| 6,293,956 B1 | * | 9/2001 | Crainich et al. | ............. | 606/155 |
| 6,464,710 B1 | * | 10/2002 | Foster | ......................... | 606/158 |
| 2002/0045909 A1 | * | 4/2002 | Kimura et al. | ............... | 606/151 |
| 2002/0099395 A1 | * | 7/2002 | Acampora et al. | ........... | 606/157 |
| 2002/0138086 A1 | * | 9/2002 | Sixto et al. | .................. | 606/151 |

* cited by examiner

Primary Examiner—Eduardo C. Robert
(74) Attorney, Agent, or Firm—Charles E. Baxley

(57) ABSTRACT

A gastric partition clip having a folded clip body made of stainless steel for clamping on the body of a patient's stomach to divide a stomach pouch from an upper part of the body of the stomach for enabling food eaten by the patient to pass from the esophagus to the distal stomach and the duodenum through the stomach pouch via an outlet in the stomach pouch. The clip body defines a clamping space adapted to keep the front and back body walls of the body of the stomach in a closed status without compression, and a mouth adapted to guide the front and back body walls of the stomach into the clamping space.

5 Claims, 8 Drawing Sheets

GASTRIC PARTITION CLIP

BACKGROUND OF THE INVENTION

1. Field of the Invention

The present invention relates to medical instruments and, more specifically, to a gastric partition clip for gastric partition to help the patient suffering from morbid obesity lose weight.

2. Description of the Related Art

In developed countries, so many people are overweight. A person having too much weight tends to cause diseases such as diabetes, heart problem, etc. The problem of overweight is harmful to the health. In order to control the weight, one may have to diet. However, controlling the weight by eating special food gives little help to a person suffering from morbid obesity. In this case, a gastro-intestinal bypass or gastric partition may be necessary. However a gastro-intestinal bypass may cause a mal absorption problem and result (resulting) in a nutrition disorder or even liver failure. A gastric partition is to reduce the volume of the stomach so as to minimize the meal-size (meal-5ize) achieving weight loss. A traditional gastric partition, as shown in FIG. 1, is to make a through hole in the body of the stomach, and then install nails to the body of the stomach in four lines to partition a stomach pouch about 5–30 ml having an opening of diameter about 10 mm, and then fix the opening with a gore-tex or marlex belt. This method limits the amount of food taken into the stomach. However, this method is complicated, takes much time, causes much pain, puts the patient to the chance of side effects including leakage and wound infection. Furthermore, when a gastric partition is done, the stomach cannot be resumed to its former status.

SUMMARY OF THE INVENTION

The present invention has been accomplished under the circumstances in view. It is therefore the main object of the present invention to provide a gastric partition clip, which simplifies the performance of gastric partition without causing a significant bleeding or severe pain. It is another object of the present invention to provide a gastric partition clip, which reduces the chance of leakage during a gastric partition. It is still another object of the present invention to provide a gastric partition clip, which does not affect the circulation of blood in the stomach after finish of the gastric partition. It is still another object of the present invention to provide a gastric partition clip, which does not cause the tissues of the stomach to decay, or the clamped area of the body of the stomach to scab. To achieve these and other objects of the present invention, the gastric partition clip comprises a folded clip body for clamping on the body of a patient's stomach to divide a stomach pouch from an upper part of the body of the stomach for enabling food eaten by the patient to pass from the esophagus to the duodenum through the stomach pouch via an outlet in the stomach pouch. The clip body comprises a clamping space adapted to keep the front and back body walls of the body of the stomach in a closed status with minimal compression, a mouth adapted to guide the front and back body walls of the stomach into the clamping space, and an arched convex portion outwardly projecting from one side of the clamping space and defining the outlet.

DETAILED DESCRIPTION OF THE PREFERRED EMBODIMENT

Figure 1:
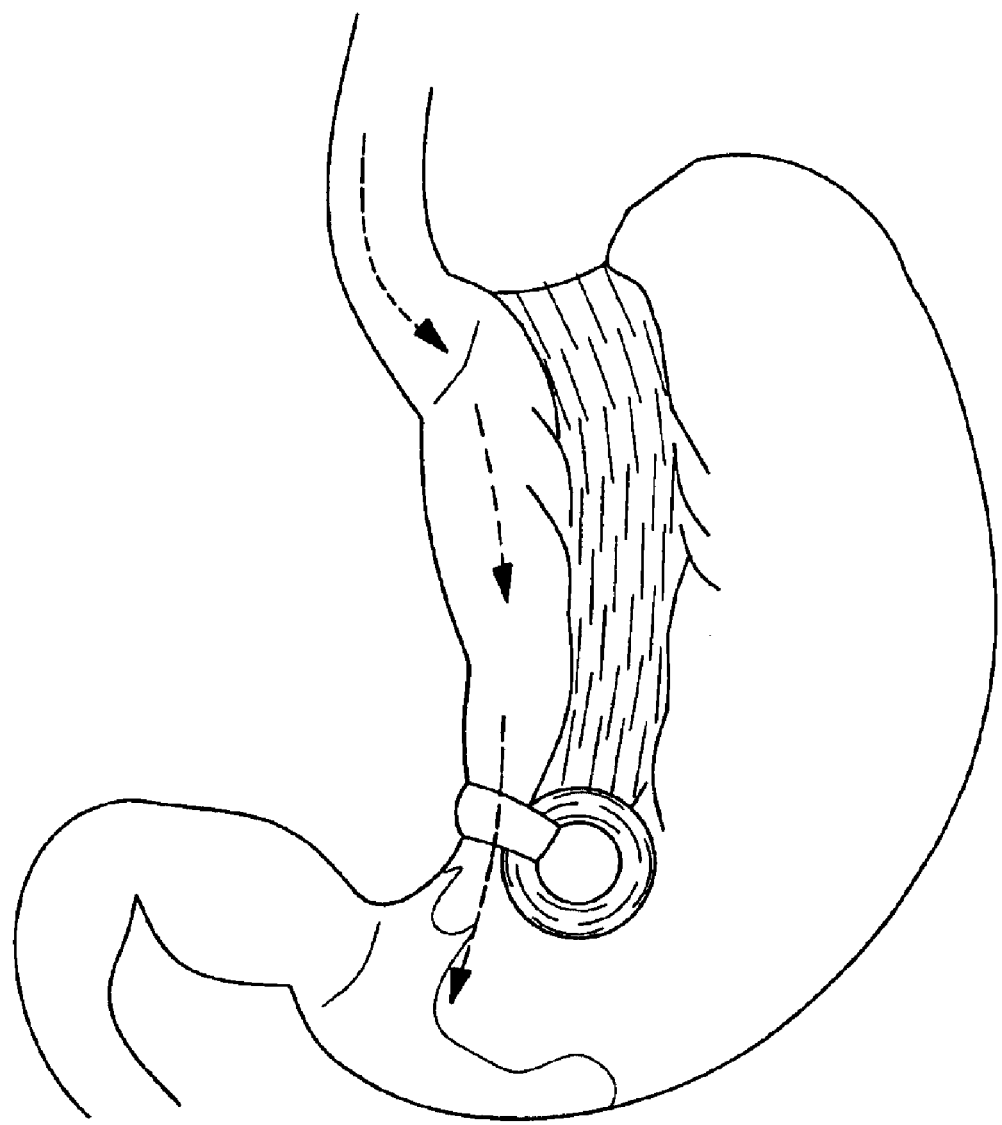
FIG. 1 is a schematic drawing showing a destructive gastric partition according to the prior art.
Figure 2:
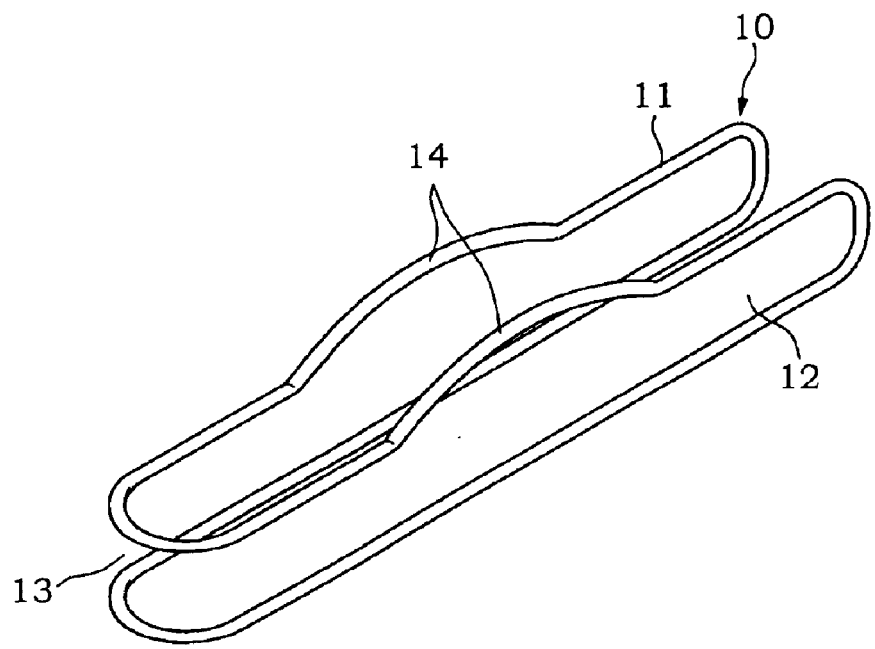
FIG. 2 is an elevational view of a gastric partition clip according to the first embodiment of the present invention.
Figure 3:
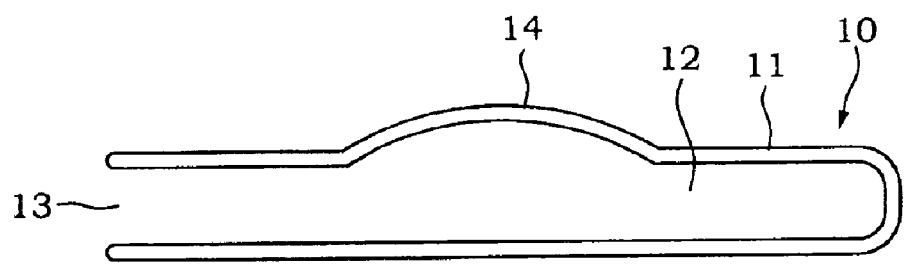
FIG. 3 is a front view of the gastric partition clip according to the first embodiment of the present invention.
Figure 7:
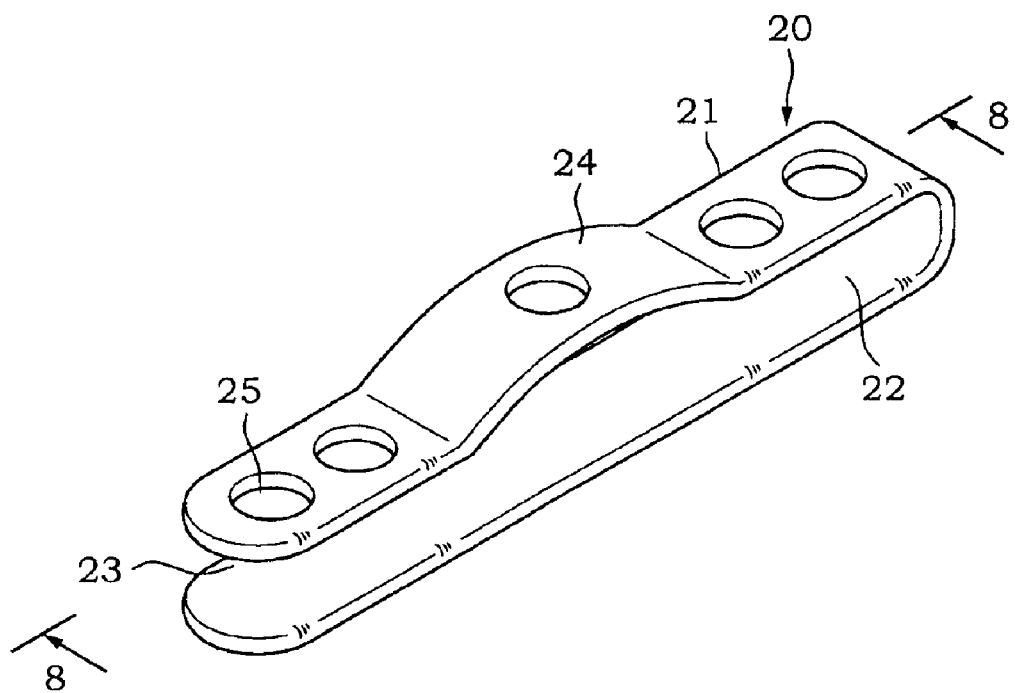
FIG. 7 is an elevational view of a gastric partition clip according to the second embodiment of the present invention.
Figure 8:
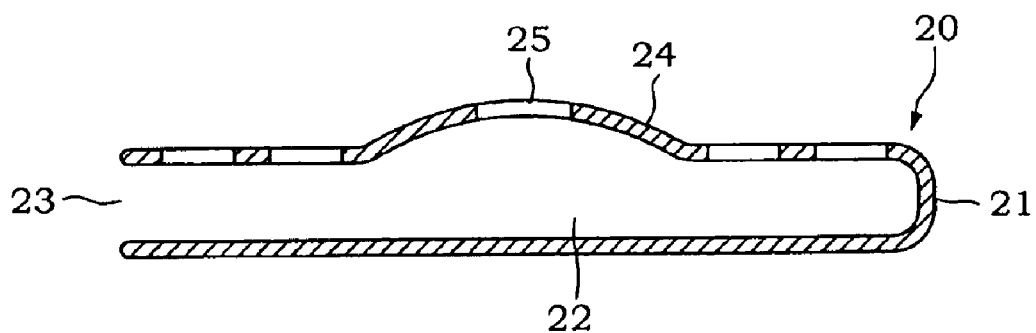
FIG. 8 is a sectional view taken along line 8—8 of FIG. 7.

Referring to FIGS. 2, 3, 7, and 8, a gastric partition clip 10 or 20 is shown comprising an integrated clip body 11 or 12 made of stainless steel for the advantage of being friendly to body tissues. The clip body 11 or 12 is folded up, defining a clamping space 12 or 22 and a mouth 13 or 23. The mouth 13 or 23 is adapted to guide the front and back body walls of the body of the stomach going to receive a gastric partition into the clamping space 12 for enabling the front and back body walls of the body of the stomach to be maintained in the clamping space 12 in a closed status to receive the treatment without compression. The clip body 11 or 12 can be an open frame formed of an endless stainless steel wire rod as shown in FIG. 2, or a solid member formed of a narrow elongated stainless steel plate as shown in FIG. 7. Further, the clip body 11 or 21 has an arched convex portion 14 or 24 outwardly projecting from one side of the clamping space 12 or 22. According to the embodiment shown in FIG. 2, the clip body 21 has a plurality of through holes 25.

Figure 4:
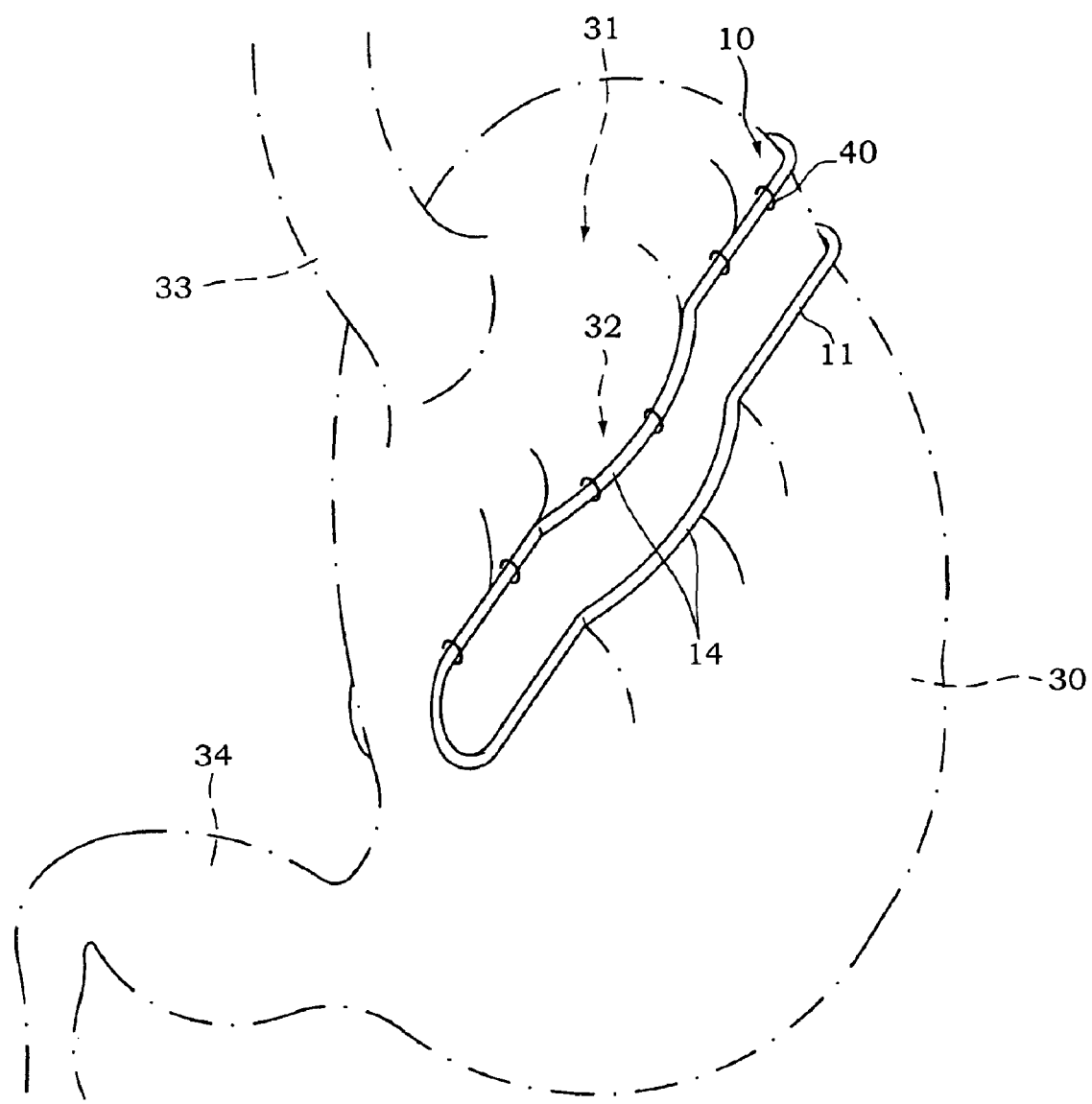
FIG. 4 is a schematic drawing showing an application example of the gastric partition clip according to the first embodiment of the present invention.
Figure 5:
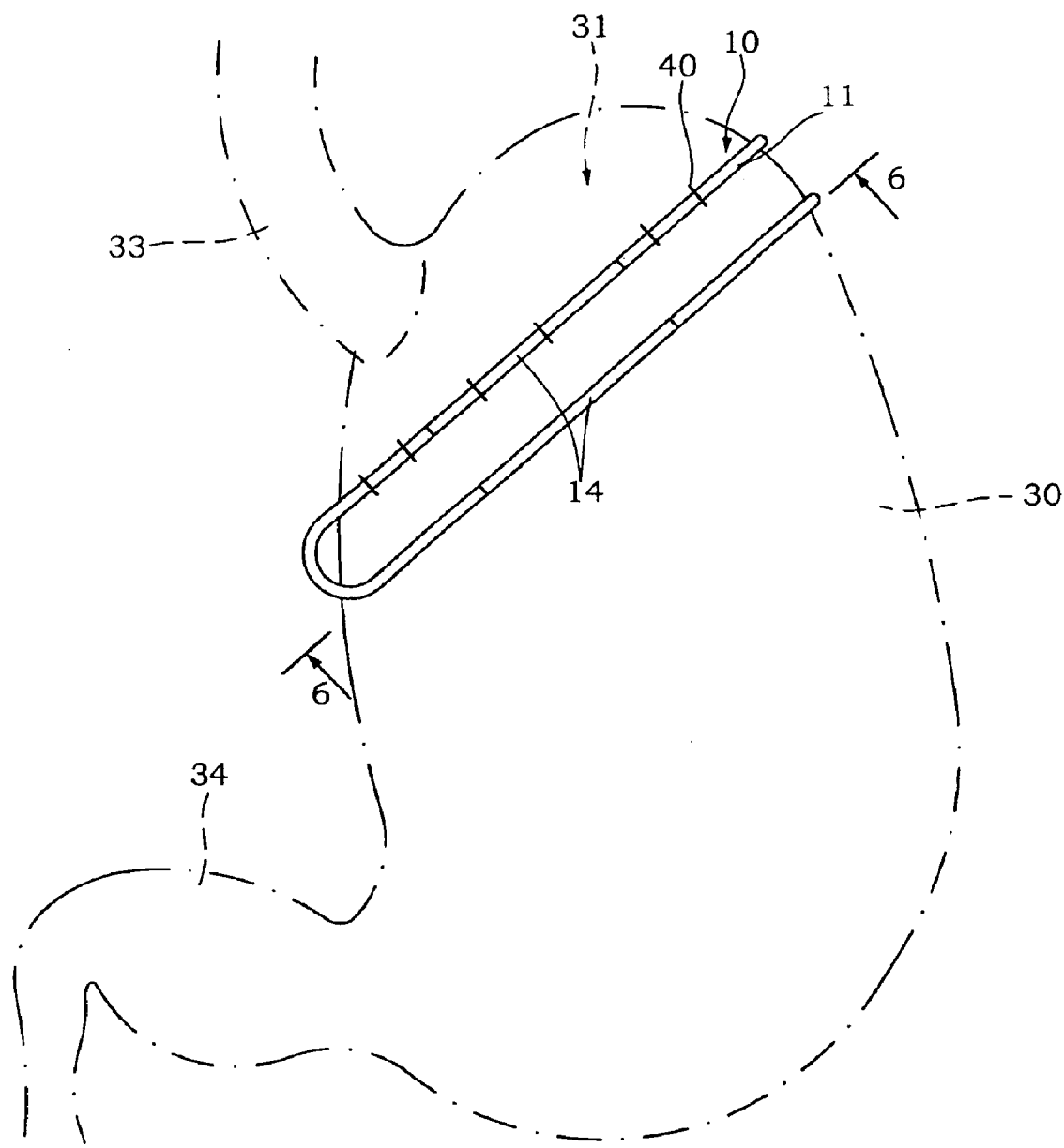
FIG. 5 is a plain view of FIG. 4.
Figure 6:
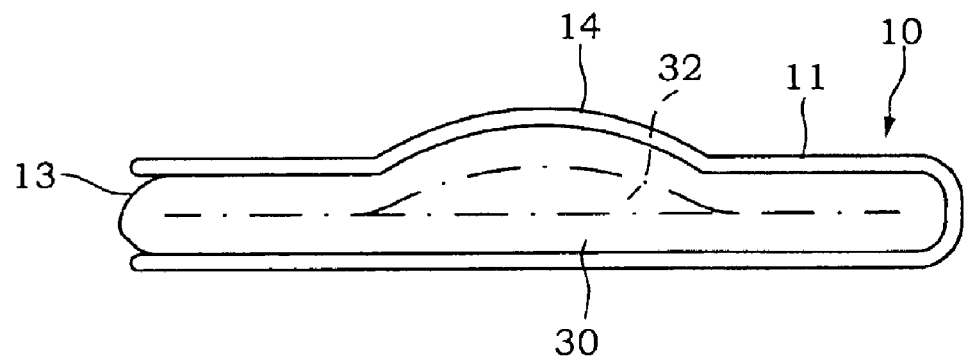
FIG. 6 is a sectional view taken along line 6—6 of FIG. 5.
Figure 11:
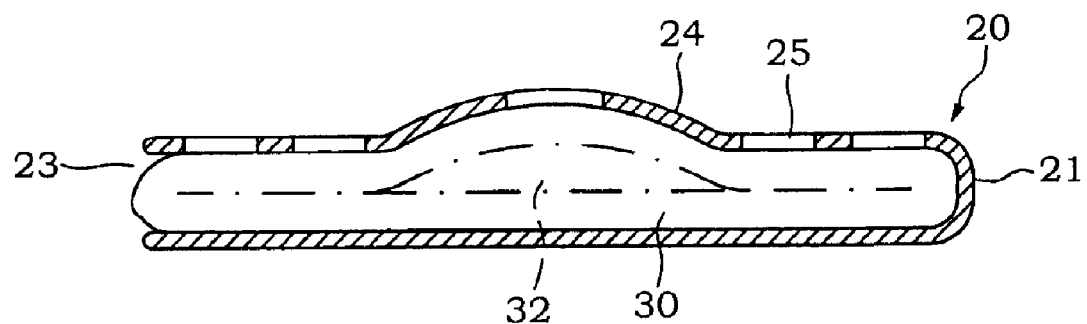
FIG. 11 is a sectional view taken along line 11—11 of FIG. 10.
Figure 9:
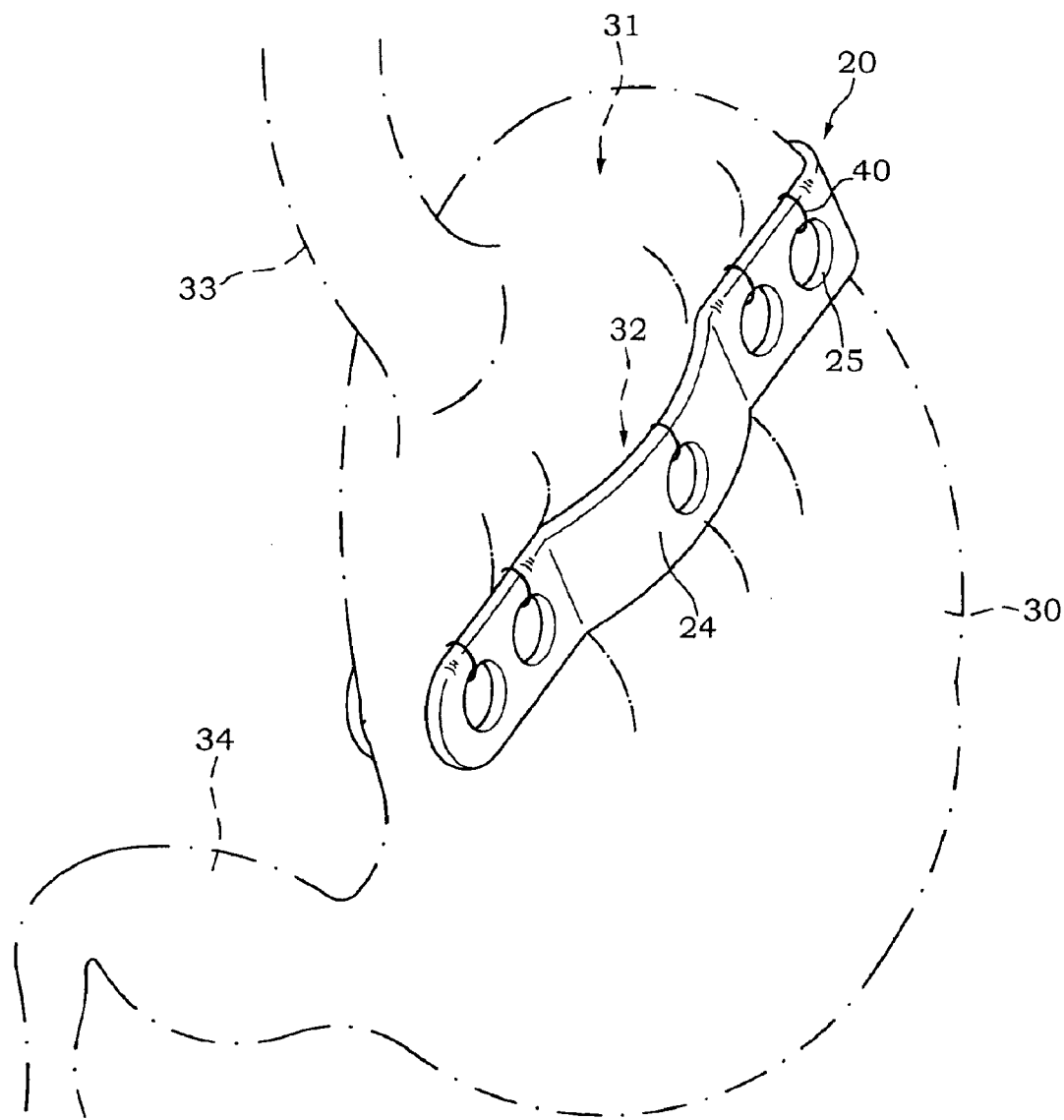
FIG. 9 is a schematic drawing showing the gastric partition clip fastened to the body of the stomach according to the second embodiment of the present invention.
Figure 10:
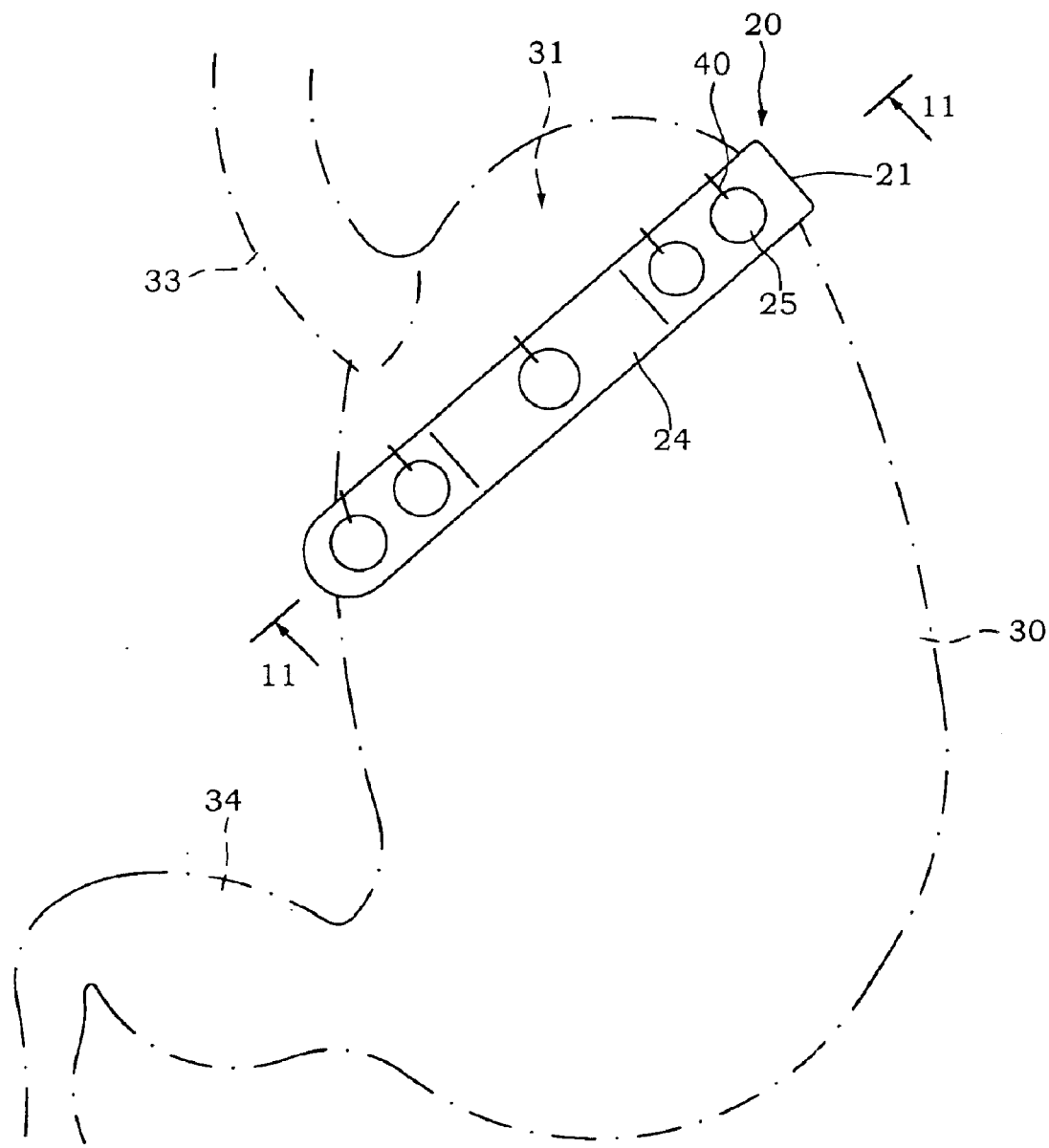
FIG. 10 is a plain view of FIG. 9.

Referring to FIGS. 4 and 9, the gastric partition clip 10 or 20 is inserted with an laparoscope into the patient's body, and then obliquely clamped on the body 30 of the stomach, keeping the front and back body walls of the body 30 of the stomach to be maintained in the clamping space 12 in a closed status without compression for free circulation of blood through the body 30 of the stomach. The gastric partition clip 10 or 20 divides a stomach pouch 31 about 30 ml from the body 30 of the stomach. After gastric partition, only a small amount of food is allowed to pass from the esophagus 33 into the stomach pouch 31 and then to pass out of the stomach pouch 31 into the distal stomach and the duodenum 34 through an outlet 32.

In comparison with conventional destructive gastric partition techniques, the invention has advantages as follows:

1. The physical gastric partition of the invention enables the gastric partition clip 10 or 20 to be removed from the body of the stomach a certain time after the treatment when desired.

2. Because the gastric partition clip 10 or 20 is fastened to the body of the stomach by means of a laparoscope, the gastric partition can be quickly finished without causing a significant bleeding or severe pain and, reducing the chance of contamination.

3. The gastric partition clip 10 or 20 keeps the front and back body walls of the stomach in a closed status without giving a compressive pressure to the front and back body walls of the body of the stomach, therefore the circulation of blood continues smoothly and, no damage is caused to the tissues of the stomach.

4. Because the gastric partition clip 10 or 20 does not give a significant compressive pressure to the front and back body walls of the stomach, the use of the clip 10 or 20 does not cause significant hypoxic injury to the tissues of the stomach.

5. The wire rod structure or the gastric partition clip 10 or the through holes 25 of the gastric partition clip 20 enables the gastric partition clip 10 or 20 to be fixedly secured to the front wall of the body of the stomach by stitches 40.

6. Simply by clamping the gastric partition clip 10 or 20 on the front and back body walls of the body of the stomach, a gastric partition is done. When necessary, the gastric partition clip 10 or 20 can be fixedly secured to the front body wall of the body of the stomach by stitches 40. This gastric partition procedure is simple and easy, and needs less time to finish.

A prototype of gastric partition clip has been constructed with the features of FIGS. 2~11. The gastric partition clip functions smoothly to provide all of the features discussed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A gastric partition clip for clamping onto the stomach of a patient and dividing the stomach of the patient into an upper part communicating with the esophagus of the patient and a lower part communicating with the duodenum of the patient while reducing an amount of communication between the upper part of the stomach of the patient and the lower part of the stomach of the patient, said clip comprising a folded clip body;

wherein said folded clip body has a clamping space;

wherein said folded clip body has a mouth;

wherein said folded clip body has an arched convex portion;

wherein said clamping space of said folded clip body is adapted to keep the front and back walls of the stomach of the patient in a closed status with minimal compression;

wherein said mouth of said folded clip body is adapted to guide the front and back walls of the stomach of the patient into said clamping space of said folded clip body;

wherein said arched convex portion of said folded clip body projects outwardly from one side of said clamping space of said folded clip body;

wherein said arched convex portion of said folded clip body is adapted to keep the front and back walls of the stomach of the patient in an open status allowing food eaten by the patient to pass from the upper part of the stomach of the patient to the lower part of the stomach of the patient; and wherein said arched convex portion of said folded clip body does not form part of an end of said folded clip body so as to divide said clamping space of said folded clip body into more than one clamping area.

2. The clip as defined in claim 1, wherein said folded clip body is an open frame formed of an endless wire rod.

3. The clip as defined in claim 1, wherein said folded clip body is formed of a strip member.

4. The clip as defined in claim 3, wherein said folded clip body has a plurality of through holes.

5. The clip as defined in claim 1, wherein said folded clip body is made of stainless steel.

* * * * *